(12) United States Patent
Drapkin (10) Patent No.: US 6,193,657 B1
(45) Date of Patent: Feb. 27, 2001

(54) IMAGE BASED PROBE POSITION AND ORIENTATION DETECTION

(75) Inventor: Evgeny Drapkin, Haifa (IL)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/224,026

(22) Filed: Dec. 31, 1998

(51) Int. Cl.$^7$ .............................. A61B 8/00; G09B 9/00
(52) U.S. Cl. ..................... 600/437; 434/262; 600/407
(58) Field of Search ..................... 600/437, 443, 600/447; 128/916; 73/1.87; 434/262, 67, 274

(56) References Cited

U.S. PATENT DOCUMENTS

| | | | |
|---|---|---|---|
| 5,127,409 | * 7/1992 | Daigle | 600/443 |
| 5,447,154 | * 9/1995 | Cinquin et al. | 600/437 |
| 5,538,004 | * 7/1996 | Bumber | 128/916 X |
| 5,540,229 | * 7/1996 | Collet-Billon | 128/916 X |
| 5,575,286 | * 11/1996 | Weng et al. | 600/454 |
| 5,609,485 | * 3/1997 | Bergman et al. | 128/916 |
| 5,655,535 | * 8/1997 | Friemel et al. | 600/443 |
| 5,769,079 | * 6/1998 | Hossock | 600/454 |
| 5,782,766 | * 7/1998 | Weng et al. | 600/443 |
| 5,810,009 | * 9/1998 | Holupka et al. | 600/439 |
| 5,827,942 | * 10/1998 | Madsen et al. | 73/1.82 |
| 5,924,989 | * 7/1999 | Polz | 600/443 |
| 6,014,473 | * 1/2000 | Hossack et al. | 600/443 |
| 6,045,508 | * 4/2000 | Hossock et al. | 600/447 |
| 6,048,317 | * 4/2000 | Longguth | 600/407 |
| 6,076,008 | * 6/2000 | Bucholz | 600/427 |

* cited by examiner

Primary Examiner—Francis J. Jaworski
(74) Attorney, Agent, or Firm—McAndrews, Held & Malloy; Christian G. Cabou; Phyllis Y. Price (57) ABSTRACT

An imaging system and method for determining sensor position and orientation with respect to an object having a known three dimensional structure is disclosed. The sensor acquires an image of the known structure. Position and orientation of the sensor is determined by processing the image with formulas corresponding to the known structure. One embodiment of the present invention comprises an ultrasound training system and method for determining the position and orientation of an ultrasound probe with respect to a known three dimensional structure embodied in an ultrasound phantom. The ultrasound probe acquires a cross sectional or partial volume image of the ultrasound phantom. The image is processed to obtain a number of geometrical image parameters. Position and orientation of the ultrasound probe are calculated from the image parameters using formulas based on the known three dimensional structure. The determination of probe position and orientation may be enhanced using image de-correlation techniques.

27 Claims, 5 Drawing Sheets

IMAGE BASED PROBE POSITION AND ORIENTATION DETECTION

CROSS-REFERENCE TO RELATED APPLICATIONS

None.

STATEMENT REGARDING FEDERALLY SPONSORED RESEARCH OR DEVELOPMENT

Not applicable.

BACKGROUND OF THE INVENTION

The present invention relates to ultrasound systems which measure and image anatomical structures. More particularly, the present invention relates to a method and apparatus for detecting the position and orientation of an ultrasound probe with respect to an ultrasound phantom, to be used in an ultrasound training system.

Ultrasound imaging systems are highly complex and sophisticated devices. System operators must be specially trained in the operation of ultrasound imaging systems in order to ensure that accurate and useful information is obtained. Training systems that provide feedback on operator technique would be useful in the training of ultrasound system operators.

Knowledge of the position and orientation of a sensor relative to a known coordinate system is useful in various fields such as in medical imaging. For example, because proper ultrasound visualization depends upon probe position and orientation, the detection of the position and orientation of an ultrasound probe relative to an imaged object is useful in an ultrasound training system.

Currently systems utilize positioning devices that are based on magnetic fields, optics or special electronic devices. For example, U.S. Pat. No. 5,609,485 discloses a system that may be used for ultrasound training wherein position and orientation information is utilized. In this system, the position and angle of an ultrasound probe (or a simulated probe) is detected by a separate positioning device that operates independently of the ultrasound system. This positioning device utilizes a transmitter/receiver pair having three antennae each that operate on magnetic field principals. The transmitter is mounted on or near a human body or mannequin while the receiver is located on the probe. When used in connection with a real ultrasound system in a data collection mode, the position information generated by the positioning device is stored in a virtual ultrasound database along with ultrasound image information corresponding to the detected position of the probe. When used in connection with a simulated ultrasound system for training, the position information is monitored and a simulated ultrasound image is simultaneously displayed using information from the virtual ultrasound database that corresponds to the position of a simulated probe.

A disadvantage of using independently operating positioning devices such as the kind described above is that use of separate positioning hardware adds to the level of complexity and cost of the system, such as an ultrasound training system. A further disadvantage is that the magnetic field used to detect probe position may interfere with, or be affected by, the imaging equipment. Still further, such positioning devices only measure position with respect to the transmitter, which is mounted on or near the imaged object. If the transmitter is not mounted in a proper position with respect to the imaged object, the probe position indicated by the positioning device may be different from the actual probe position.

A need remains for an improved manner of detecting probe position and orientation to overcome the above-identified difficulties. It is an object of the present invention to meet this need.

SUMMARY OF THE INVENTION

It is an object of the preferred embodiment of the present invention to provide an imaging system that is capable of determining sensor position and orientation.

It is a further object of the preferred embodiment of the present invention to provide an ultrasound system that is capable of determining ultrasound probe position and orientation.

It is a further object of the preferred embodiment of the present invention to provide an ultrasound training system that is capable of providing probe position and orientation feedback to the system operator.

It is another object of the preferred embodiment of the present invention to provide an ultrasound system that is capable of determining probe position and orientation without the use of a separate positioning device and associated hardware.

It is another object of the preferred embodiment of the present invention to provide an imaging system that provides sensor position and orientation information in an efficient and economical manner.

These and other objects of the present invention are provided by a system and method for determining sensor position and orientation with respect to an object having a known three dimensional structure. The sensor acquires an image of the known structure. Position and orientation of the sensor is determined by processing the image with formulas corresponding to the known structure.

One embodiment of the present invention comprises an ultrasound training system and method for determining the position and orientation of an ultrasound probe with respect to a known three dimensional structure embodied in an ultrasound phantom. An ultrasound phantom is generally a block of material suitable for imaging by an ultrasound system. The ultrasound probe acquires a cross sectional or partial volume image of the ultrasound phantom. The image is processed to obtain a number of geometrical image parameters. Position and orientation of the ultrasound probe is calculated from the image parameters using formulas based on the known three dimensional structure.

The three dimensional structure of the above described ultrasound phantom may be designed such that for each position and orientation of the ultrasound probe, located on or above the upper face of the phantom, a unique ultrasound image is acquired. Such structure may comprise a number of planes of a material embedded within the ultrasound phantom that will provide an ultrasound echo characteristic that sharply contrasts with that of the remaining phantom material.

The above described system and method may employ an image de-correlation algorithm to enhance the detection of small changes in probe position and orientation. Error accumulations created by de-correlation may be avoided by reevaluating the results obtained from the original calculation of probe position and orientation.

The above described system and method of determining sensor position and orientation with respect to an object with a known structure can be applied in other applications such as in radar, sonar or video capturing systems.

Other objects, features, and advantages of the present invention will be apparent from the accompanying drawings and from the detailed description that follows below.

DETAILED DESCRIPTION OF THE PREFERRED EMBODIMENT

A method and apparatus are described for determining the position and orientation of an ultrasound probe with respect to an ultrasound phantom. In the following description, numerous specific details are set forth in order to provide a thorough understanding of the preferred embodiment of the present invention. It will be apparent, however, to one of ordinary skill in the art that the present invention may be practiced without these specific details.

Figure 1:
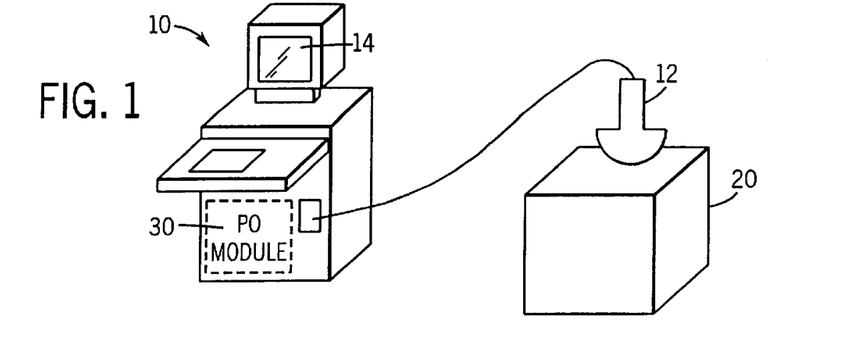
FIG. 1 illustrates an ultrasound training system according to a preferred embodiment of the present invention.
Figure 2:
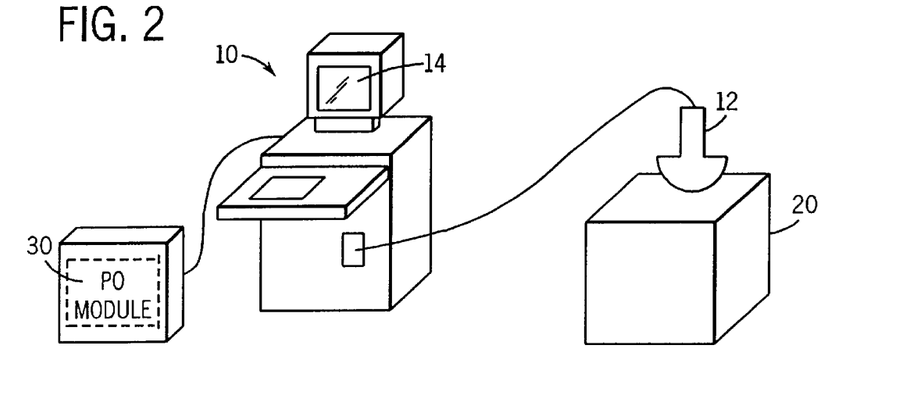
FIG. 2 illustrates an ultrasound training system according to a preferred embodiment of the present invention.

An ultrasound system according to a preferred embodiment of the present invention is shown in FIG. 1. Ultrasound system 10 acquires an image via ultrasound probe 12 of an ultrasound phantom 20 by employing conventional ultrasound imaging techniques. For example, ultrasound system 10 may acquire image information by transmitting a series of ultrasound waves into the ultrasound phantom 20 and then detecting the ultrasound echoes reflected therefrom. The ultrasound system 10 may acquire a number of two-dimensional sub-sections or pixels (for example, 256×256) within an image frame comprising a slice or cross section of the phantom 20 within the plane of the ultrasound beam. The ultrasound system 10 then displays the image information, such as in a B-mode image. Typically, echo value data for each image frame is processed and displayed on video monitor 14 by converting the echo value datum for each pixel into a value indicating display brightness. According to the preferred embodiment of the present invention, the echo value data for each image frame is alternatively (or additionally) processed by a position and orientation module 30 (referred to herein as "PO module"). PO module 30 may comprise hardware and/or software operating within ultrasound system 10, or, as illustrated in FIG. 2, may comprise hardware and/or software within a separate unit that can be connected to ultrasound system 10.

According to the preferred embodiment of the present invention, the ultrasound phantom 20, as more fully explained herein, contains an internal three dimensional structure. The size and shape of the internal three dimensional structure, including distances and angles between structural elements, are known to the ultrasound system 10. These known quantities are referred to herein as geometric characteristics.

After the ultrasound system 10 acquires an ultrasound image via probe 12, PO module 30, as more fully explained herein, processes the echo value data for each image frame by first obtaining through image processing a number of geometrical image parameters corresponding to angles and distances between structural lines within the image frame. The position and orientation of probe 12 with respect to the phantom 20 is then calculated from the obtained image parameters using predetermined formulas and geometric characteristics that correspond to the known three dimensional structure within the phantom 20. The result of the calculation of position and orientation may be enhanced by using image de-correlation techniques to detect small changes in position and orientation. The output of PO module 30 is the position and orientation of probe 12 with respect to a coordinate system associated with phantom 20. The output information may be displayed on display 14 and/or may be used for other purposes. For example, stored ultrasound images of real anatomical structures could be displayed according to the determined probe position and orientation to simulate an ultrasound scanning session.

Figure 3:
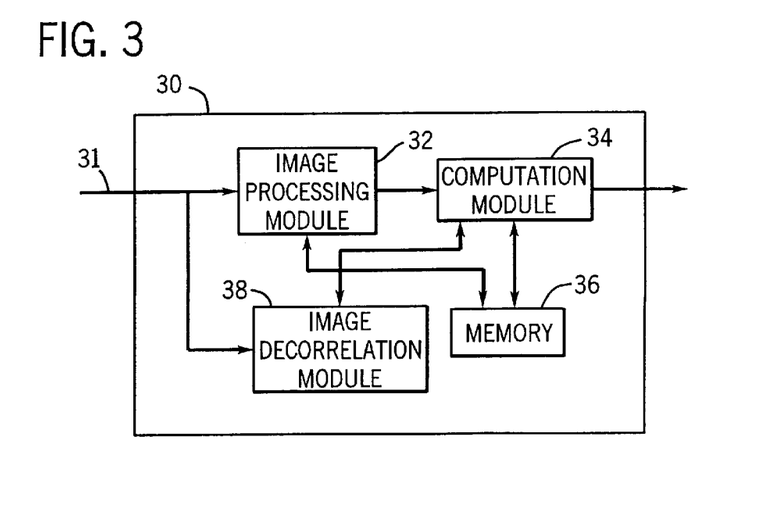
FIG. 3 illustrates a block diagram of a position and orientation module of an ultrasound training system according to a preferred embodiment of the present invention.

FIG. 3 illustrates a PO module 30. PO module 30 includes an image processing module 32, a computation module 34 and a memory 36, and may include an image de-correlation module 38. The image processing module 32 receives echo value data from the ultrasound system 10 over line 31 and performs image processing on each image frame of echo value data to obtain a set of image parameters. Information, such as geometric characteristics and formula, stored in memory 36 is used by the image processing module 32 to identify, in each image frame, elements of the internal structure of the phantom 20. The image parameters determined by the image processing module 32, and geometric characteristics and formulas stored in memory 36 are then used by the computation module 34 to calculate the current probe position and orientation. Optimally, the image de-correlation module 38 may be used to enhance the accuracy of the probe position and orientation determined by the computation module 34 by processing successive image frames using known image de-correlation techniques. The output of PO module 30 is the current position and orientation of the probe with respect to the imaged structure.

Figure 4:
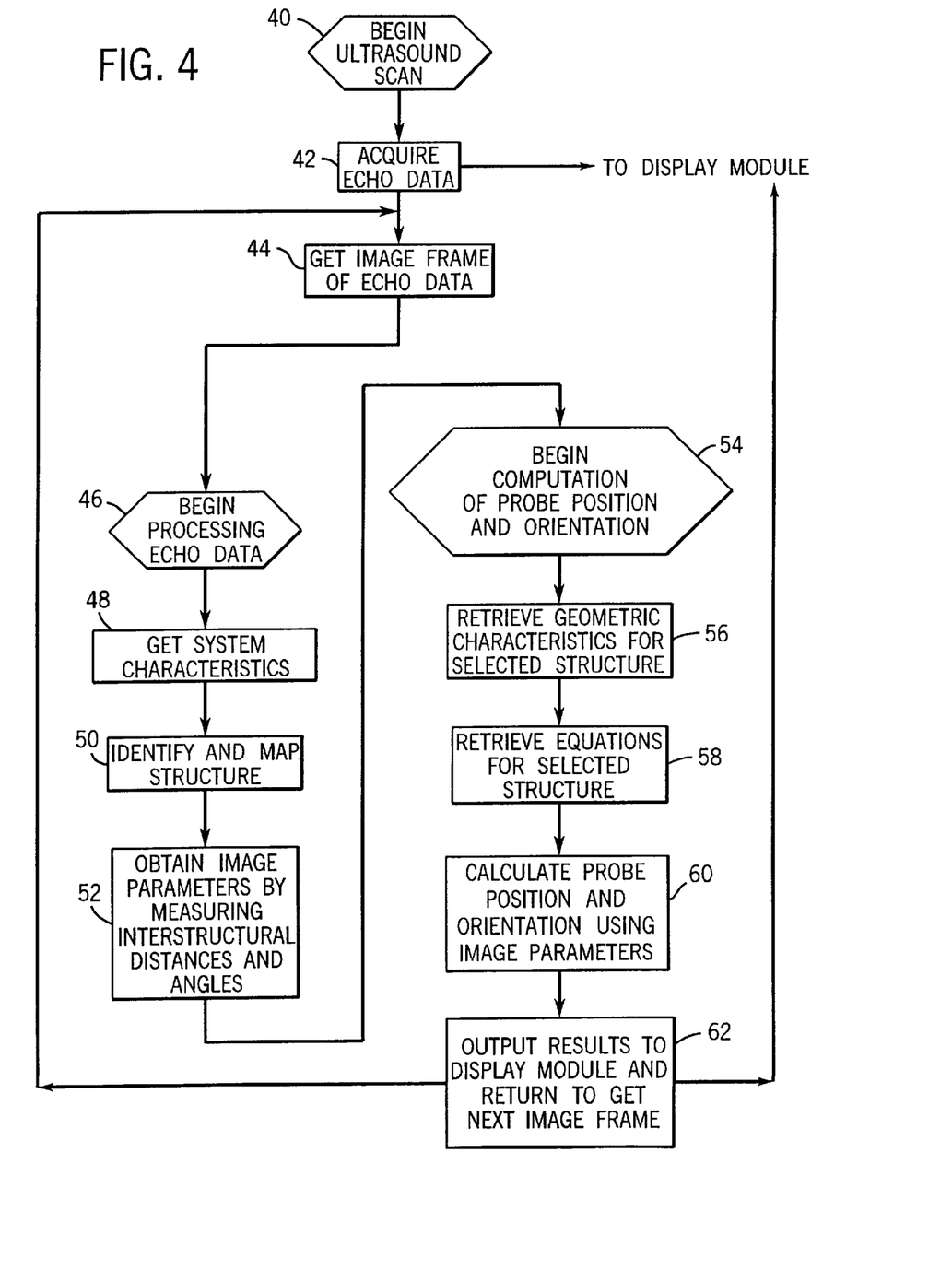
FIG. 4 illustrates a flow chart of a process for determining position and orientation of a probe in an ultrasound training system according to a preferred embodiment of the present invention.

FIG. 4 is a flow chart of an exemplary procedure carried out by the ultrasound system 10 for determining probe position and orientation according to the preferred embodiment of the present invention. An ultrasound scanning session is initiated (step 40) and echo data is acquired (step 42) by passing the ultrasound probe over the object to be imaged. The acquired ultrasound data is sent to the display module for further processing and display. The acquired echo data is also sent to the PO module 30. The PO module 30 obtains an image frame of echo data (step 44) and begins the image processing routine (step 46). First the current system characteristics are detected by image processing module 32 (step 48). For example, the type of probe, scan depth, focal zone and gain may be considered. Next, elements of the internal structure of the imaged object (phantom) are identified and mapped by the image processing module 32 (step 50). Structural elements will appear as a series of lines within the image frame. Individual lines are recognized by the image processing module 32 as corresponding to a specific structural element based on predetermined knowledge of the internal structure. For example, the thickness of a structural element, the use of parallel duplicate structures and/or the arrangement of the structure may be used by the image processing module 32 to distinguish one structural element from another. The lines may be defined with respect to a two dimensional coordinated system in the plane of the ultrasound scan with one axis of the coordinate system parallel to the probe's center axis. The origin of the coordinate system may be at a point on the probe face along the probe's center axis. Once the lines are identified and mapped by the image processing module 32, the image parameters are obtained by image processing module 32 by measuring interstructural distances and angles (step 52). The obtained image parameters are the sent to the computation module 34 to begin the computation of probe position and orientation (step 54). The computation module 34 retrieves from memory 36 the geometric characteristics (step 56) and the appropriate equations (step 58) that correspond to the structure being imaged. Next, the computation module 34 calculates the probe position and orientation using the obtained image parameters, the geometric characteristics and the equations (step 60). Finally, the calculated probe position and orientation are output to the display module and the program returns to begin processing the next image frame (step 62). This process is repeated continuously to update the output as the probe position and orientation changes between frames during an ultrasound scanning session.

As an alternative to the above described calculation step, the position and orientation of the probe may be pre-calculated for all possible sets of image parameters. The pre-calculated position and orientation data may be stored in a look-up table. Each time a set of image parameters is obtained, the look-up table may be accessed and the position and orientation data corresponding to the presently acquired image parameters may be selected for output.

Because the above described calculation of probe position and orientation may be insensitive to very small position and orientation changes, the PO module 30 may also include an image de-correlation module 38 comprising hardware and/or software. The image de-correlation module 38 processes the ultrasound image using a known image de-correlation algorithm. An example of an image de-correlation algorithm is described in U.S. Pat. No. 5,655,535. Image de-correlation is based upon a known property of the ultrasound modality that states that good correlation exists between consecutive images. Any error accumulations created by de-correlation may be avoided by reevaluating the results obtained from the original calculation of probe position and orientation.

The ultrasound phantom 20 of the preferred embodiment of the present invention has a known three dimensional internal structure that preferably provides a unique cross section for all planes intersecting the upper and lower surface of the phantom 20. An example of such a three dimensional structure is described with respect to FIGS. 5, 6a and 6b. The phantom 20 itself may generally be any size and shape, such as that of a human body. For simplicity, however, a simple rectangular or cubic shape has been selected herein for illustrating ultrasound phantom 20. The phantom 20 may be made of any material suitable for ultrasound imaging and is preferably rigid so as to maintain its shape and the geometric relations of its internal structure. The internal structure may be formed of a material that will provide an ultrasound echo characteristic that sharply contrasts with that of the remaining phantom material.

Figure 5:
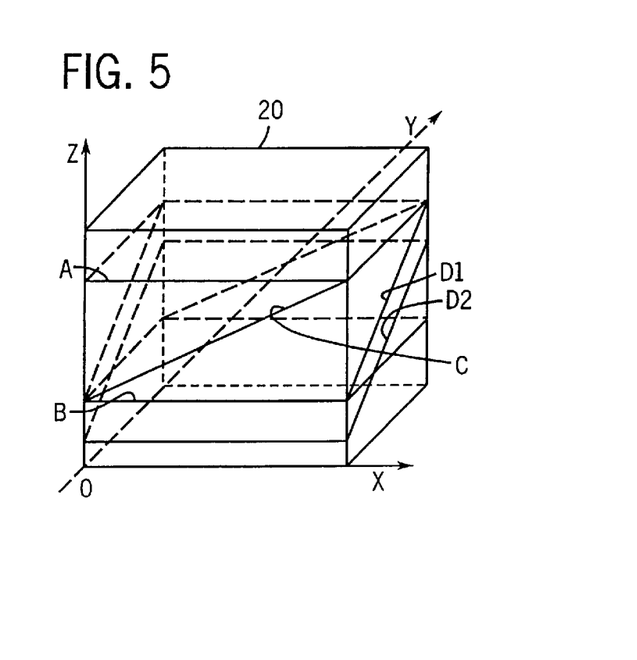
FIG. 5 illustrates an orthogonal view of an exemplary ultrasound phantom according to a preferred embodiment of the present invention.
Figure 6A:
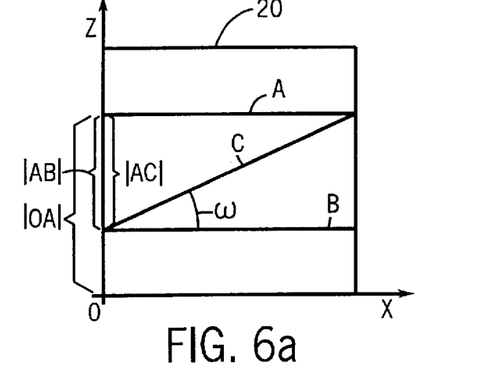
FIG. 6a illustrates a cross sectional view in the ZOX plane of the exemplary ultrasound phantom of FIG. 5 according to a preferred embodiment of the present invention.
Figure 6B:
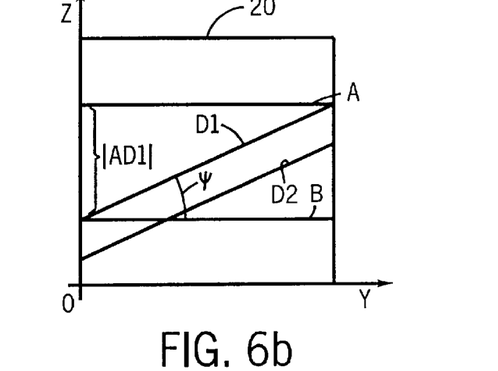
FIG. 6b illustrates a cross sectional view in the ZOY plane of the exemplary ultrasound phantom of FIG. 5 according to a preferred embodiment of the present invention.

An exemplary embodiment of the ultrasound phantom 20 and its internal structure is illustrated in FIGS. 5, 6a and 6b. FIG. 5 is an orthogonal view of the phantom 20. FIG. 6a is a cross sectional view in the XOZ plane of the phantom 20. FIG. 6b is a cross sectional view in the YOZ plane of the phantom 20. The exemplary internal three dimensional structure has five planar structural elements. The five planar structures are labeled A, B, C, D1 and D2. Planes A and B are parallel and horizontal (i.e., parallel to the XOY plane). The distance between planes A and B is a known distance |AB|. The distance between plane A and the XOY plane is a known distance |OA|. Plane C is perpendicular to the XOZ plane and intersects with the YOZ plane and plane B by the same line parallel to the OY line and forms a known angle $\omega$ with the XOY plane. Planes D1 and D2 are parallel to each other and perpendicular to the YOZ plane. Plane D1 intersects with the YOZ plane and plane B by a line parallel to the OX line and forms a known angle $\psi$ with the XOY plane. Distance |AC| is a known distance between planes A and C at the YOZ plane and is equal to distance |AB|. Distance |AD1| is a known distance between planes A and D1 at the XOZ plane and is also equal to distance |AB|. Thus, for this exemplary internal three dimensional structure, there are four known geometric characteristics—distances |AB| and |OA| and angles $\psi$ and $\omega$.

The above described geometric characteristics may be stored in a memory 36 in the PO module 30 or may be stored separately in any known data storage medium. If a number of phantoms are available, each having its own unique set of geometric characteristics, the geometric characteristics may be stored along with an identification of the phantom to which they belong. In this case, the operator of the ultrasound system 10 would select the appropriate phantom and the corresponding geometric characteristics would be retrieved from memory 36 for use by the PO module 30.

Figure 7:
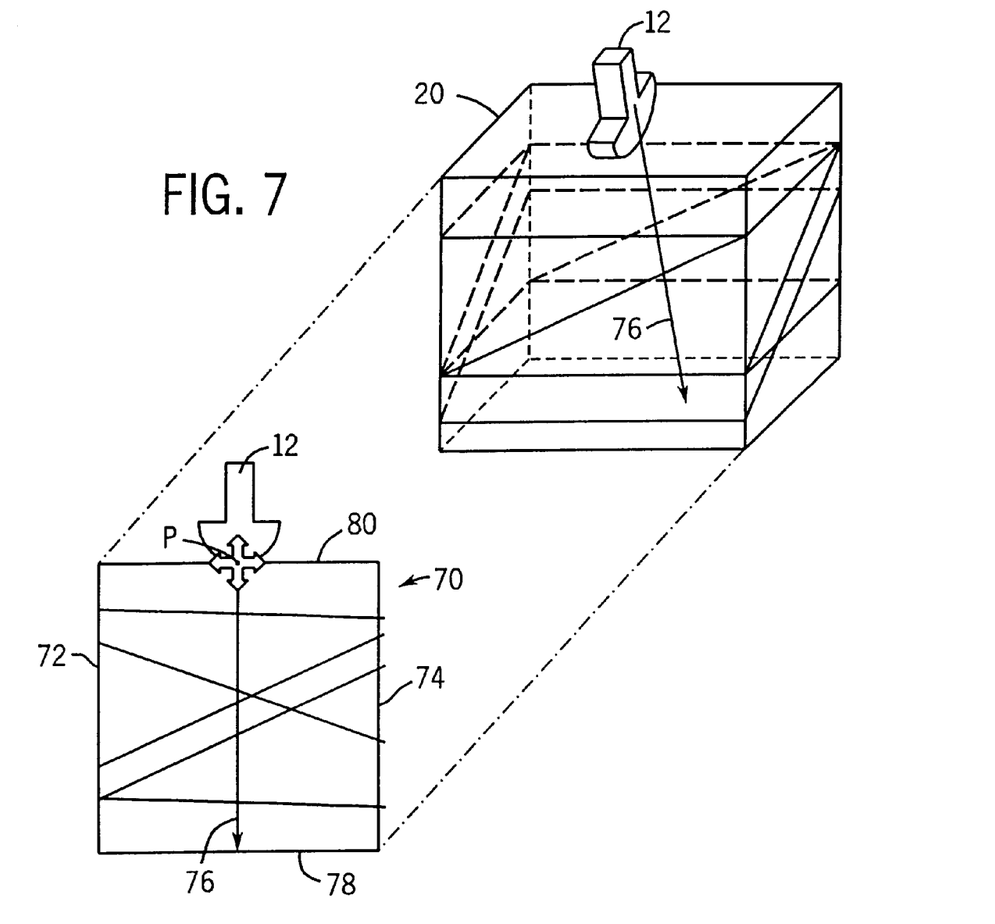
FIG. 7 illustrates an ultrasound probe in an arbitrary probe position and orientation acquiring an ultrasound image of the exemplary phantom of FIG. 5 and the corresponding acquired cross sectional image according to a preferred embodiment of the present invention.

Next, an example is described in connection with FIG. 7 to identify a probe position and orientation. The procedure of determining the position and orientation of the probe 12 begins with the acquisition of a cross sectional sector scan (or a partial volume as the case may be) of an ultrasound image of the phantom 20. FIG. 7 illustrates an orthogonal view of the phantom 20 of FIG. 5 and a cross sectional ultrasound image 70 of the phantom 20, which includes the internal structure described with respect to FIGS. 5, 6a and 6b. The cross sectional image 70 represents one image frame of echo data acquired from an arbitrary position and orientation of the probe 12. The side edges 72 and 74 of the image 70 are parallel to the focal axis 76 of the probe 12 while the upper and lower edges 78 and 80 of the image 70 are perpendicular to the focal axis 76 of the probe 12. A point labeled P indicates the intersection of the focal axis 76 and the upper edge 80. This point P also is the center point of the probe face.

Figure 8A:
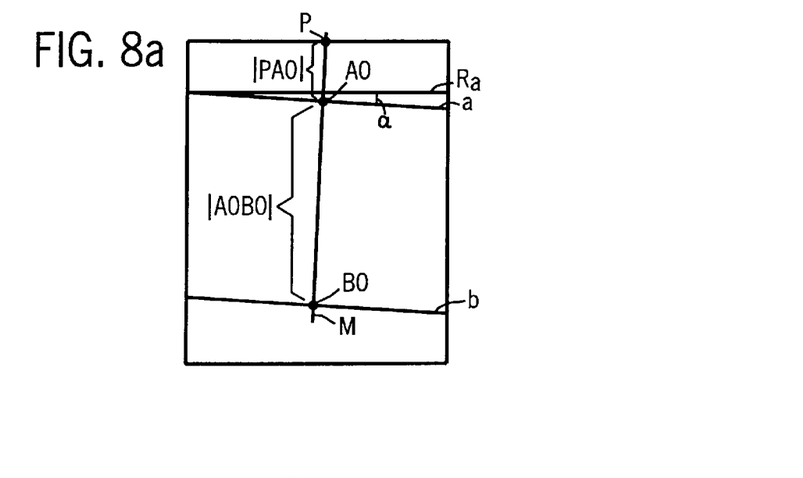
FIG. 8a illustrates a partial view of the cross sectional ultrasound image of FIG. 7 showing image parameters according to a preferred embodiment of the present invention.
Figure 8B:
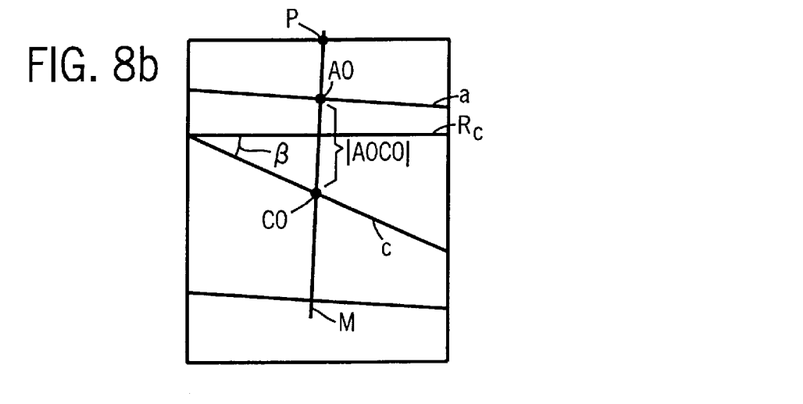
FIG. 8b illustrates a partial view of the cross sectional ultrasound image of FIG. 7 showing image parameters according to a preferred embodiment of the present invention.
Figure 8C:
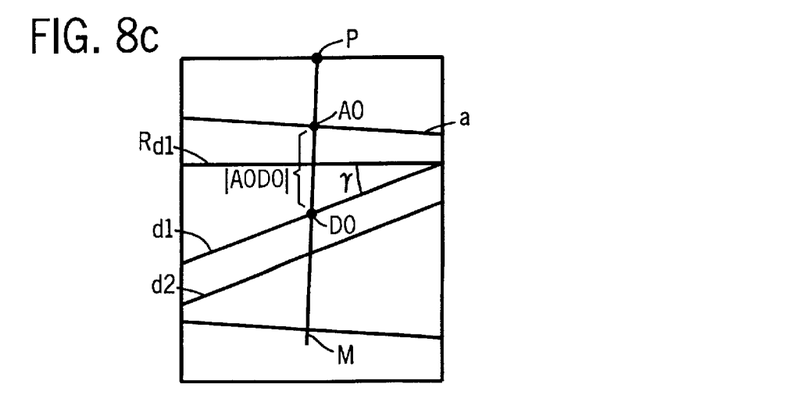
FIG. 8c illustrates a partial view of the cross sectional ultrasound image of FIG. 7 showing image parameters according to a preferred embodiment of the present invention.

To further explain the manner in which the image processing module 32 obtains image parameters, the cross sectional image 70 of FIG. 7 is broken down into three images illustrated in FIGS. 8a, 8b and 8c. FIGS. 8a, 8b and 8c illustrate exemplary image parameters that could be obtained from processing the image 70 of FIG. 7. In FIG. 8a, image processing module 32 detects line a, which is an intersection line of the scanning plane with plane A in the phantom 20. Similarly, the image processing module 32 detects line b, which is an intersection line of the scanning plane with plane B in the phantom 20. Image parameter α is the angle between line a and a reference line Ra that is parallel to the upper and lower edges 78 and 80 of the image 70 or perpendicular to the probe's focal axis 76. Line M is perpendicular to lines a and b and runs through point P. Once the image processing module 32 detects line a and line b, it calculates image parameter angle α. Next, the image processing module 32 projects line M through the image 70 and determines points A0 and B0. Point A0 is the intersection between lines a and M. Point B0 is the intersection between lines B and M. The image processing module 32 then calculates image parameter |A0B0|, which is the distance between points A0 and B0 and image parameter |PA0|, which is the distance between points P and A0.

In FIG. 8b, line c is an intersection line of the scanning plane with plane C. Image parameter β is the angle between line c and a reference line Rc perpendicular to the probes focal axis 76. Point C0 is the intersection point between lines C and M. Image parameter |A0C0| is the distance between points A0 and C0. The image processing module 32 detects line c and calculates reference line Rc and image parameter angle β. As line M is already projected through the image 70, the image processing module next determines point C0 and image parameter distance |A0C0|.

In FIG. 8c, lines d1 and d2 are the intersections lines between the scanning plane and planes D1 and D2, respectively. Image parameter γ is the angle between line d1 and a reference line Rd1 perpendicular to the probes focal axis 76. Point D0 is the intersection between lines d1 and M. Image parameter |A0D0| is the distance between points A0 and D0. The image processing module 32 detects lines d1 and d2, and calculates reference line Rd1. The image processing module 32 then calculates the image parameter angle γ, point D0 and image parameter distance |A0D0|. Thus, the image processing module 32 obtains seven image parameters—distances |A0B0|, |A0C0|, |A0D0| and |PA0| and angles α, β and γ.

The computation module 34 calculates the position and orientation of the probe 12 with respect to the phantom 20 using the seven image parameters, |A0B0|, |A0C0|, |A0D0|, |PA0|, α, β and γ, determined by the image processing module 32 along with the four known predetermined geometric characteristics |AB|, |AD1|, ψ and ω of the phantom's internal structure. Position and orientation are calculated using the following predefined equations or relationships. The "in plane" angle of the probe, φ, is defined by the following equation:

$$\phi = \alpha \quad (\text{eq. 1})$$

The "out of plane" angle of the probe, θ, is defined by the following equation:

$$\theta = \arccos(|AB|/|A0B0|) \quad (\text{eq. 2})$$

The "around the probe axis" angle, ξ is defined by the following equation:

$$\xi = \arccos(tg(\beta-\alpha)*\cos(\theta)/tg(\omega)) \quad (\text{eq. 3})$$

or may also be define by the following equation:

$$\xi = \arccos(tg(\gamma-\alpha)*\cos(\theta)/tg(\psi)) - 90° \quad (\text{eq. 4})$$

Both of the equations given for θ should provide the same result. Errors could be reduced by calculating both equations 3 and 4 and then taking their average. The X, Y and Z coordinates of the probe coordinate of the probe center are defined by the following equations:

$$X = (|AB| - |A0C0|*\cos(\theta))/tg(\omega) \quad (\text{eq. 5})$$

$$Y = (|AB| - |AD0|*\cos(\theta))/tg(\psi) \quad (\text{eq. 6})$$

$$Z = |OA| + |PA0|. \quad (\text{eq. 7})$$

Thus, the computation module 34 will provide an output of three position indicators, coordinates X, Y and Z, and three orientation indicators, angles φ, θ and ξ.

The following example provides a complete calculation of probe position and orientation based upon hypothetical geometric characteristics and image parameters: The phantom 20 includes an internal structure having the following geometric characteristics:

|OA|=10 cm
|AB|=7 cm
ω=30°
ψ=30°

The image parameters determined by the image processing module 32 are:

α=5.4°
β=31°
γ=−21.2°
|PA0|=3.5 cm
|A0B0|=8.5 cm
|A0C0|=5 cm
|A0D0|=4 cm

The six parameters (X, Y, Z, φ, θ and ξ) which characterize the probe position and orientation may be calculated by the computation module 34 in step 60 of FIG. 4 as follows:
1) φ=α=5.4°.
2) θ=arccos (|AB|/|A0B0|)=arccos (7/8.5)=34.56°
3) cos (θ)=cos(34.56)=0.82
4) β−α=31°−5.4°=26.6°
5) tg(β−α)=0.5
6) tg(ω)=tg(ψ)=tg(30°)=0.58
7) ξ1=arccos (tg(β−α)*cos(θ)/tg(ω))=arccos (0.5*0.82/0.58)=arccos (0.7)=45.6°
8) γ−α=−21.2−5.4=−26.6°
9) tg(γ−α)=−0.5
10) ξ2=arccos (tg(γ−α)*cos(θ)/tg(ψ))−90=arccos (−0.5*0.82/0.58)=arccos (0.7)−90=134.4−90=44.4°
11) ξ=(ξ1+ξ2)/2=(44.4+45.6)/2=45°
12) X coordinate of probe center=(|AB|−|A0C0|*cos(θ))/tg (ω)=(7−5*cos(34.56))/tg(30)=(7−5*0.82)/0.58 =5 cm
13) Y coordinate of probe center=(|AB|−|A0D0|*cos(θ))/tg (ψ)=(7−4*cos(34.56))/tg(30)=(7−4*0.82)/0.58=6.41 cm
14) Z coordinate of probe center=|OA|+|PA0|=10+3.5=13.5 cm Thus, for this example the probe position and orientation is defined by the parameter set (X=5 cm, Y=6.41 cm, Z=13.5 cm, φ=5.4°, θ=34.56° and ξ=45°).

In the foregoing specification the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarding in an illustrative rather than restrictive sense.

What is claimed is:

1. A method for determining a position and orientation of an ultrasound probe with respect to an ultrasound phantom in an ultrasound imaging system, the ultrasound phantom embodying a known structure and the ultrasound training system storing having a set of at least one predetermined geometric characteristic of the known structure, the method comprising:

acquiring an ultrasound image of said known structure;

processing the ultrasound image to obtain at least one image parameter; and calculating at least one of probe position and probe orientation with respect to said phantom based on the at least one image parameter and the set of at least one predetermined geometric characteristic.

2. The method according to claim 1, wherein the step of acquiring comprises:

acquiring a cross sectional image of the known structure.

3. The method according to claim 1, wherein the step of acquiring comprises:

acquiring a partial volume image of the known structure.

4. The method according to claim 1, wherein the step of calculating comprises calculating at least one of the probe position and orientation based on the known structure which comprises a number of planes of material embodied within said ultrasound phantom.

5. The method according to claim 4, wherein the step of calculating comprises calculating at least one of the probe position and orientation based on the set of at least one predetermined geometric characteristic which includes a distance between at least two of said number of planes and an angle between at least two of said number of planes.

6. The method according to claim 4, wherein the step of processing the image to obtain at least one image parameter includes measuring a distance between at least two of said number of planes and measuring an angle between at least one of said number of planes and a reference line associated with the focal axis of the probe.

7. The method according to claim 1 further comprising:

enhancing the calculation of probe position and orientation by performing image de-correlation to detect small changes in probe position and orientation.

8. The method according to claim 7 further comprising:

correcting for any error accumulations created by de-correlation by reevaluating the original calculation of probe position and orientation.

9. The method according to claim 1 further comprising:

selecting said known structure from a number of known structures and retrieving from memory the set of at least one geometric characteristic that corresponds to the selected known structure.

10. The method according to claim 1 further comprising:

displaying on a display the calculated probe position and orientation.

11. In an ultrasound training system having an ultrasound probe for acquiring images, a subsystem for determining a position and orientation of the ultrasound probe with respect to an ultrasound phantom, the ultrasound phantom embodying a known structure and the ultrasound training system storing a set of at least one predetermined geometric characteristic, the subsystem comprising:

an image processing module processing an acquired image of said known structure to obtain at least one image parameter; and a computation module calculating at least one of the probe position and probe orientation with respect to said phantom based on the at least one image parameters and the set of predetermined geometric characteristics.

12. An ultrasound imaging system according to claim 11 further comprising:

a display displaying the calculated probe position and orientation.

13. An ultrasound imaging system according to claim 11 further comprising:

a memory storing said set of at least one predetermined geometric characteristic of said known structure.

14. An ultrasound imaging system according to claim 11, wherein the known structure comprises a number of planes of material embodied within said ultrasound phantom.

15. An ultrasound imaging system according to claim 14, wherein the set of at least one predetermined geometric characteristic includes a distance between at least two of said number of planes and an angle between at least two of said number of planes.

16. An ultrasound imaging system according to claim 14, wherein the image processing module measures a distance between at least two of said number of planes and an angle between at least one of said number of planes and a reference line associated with the focal axis of the probe.

17. An ultrasound imaging system according to claim 11 further comprising:

an image de-correlation module enhancing the calculation of probe position and orientation by performing image de-correlation to detect small changes in probe position and orientation.

18. A method for determining a position and orientation of a sensor with respect to a phantom in an imaging training system, the phantom embodying a known structure and the training system storing a number of known geometric characteristics of the known structure, the method comprising:

acquiring with the sensor an image of said known structure;

processing the image to obtain a number of image parameters; and calculating the sensor position and orientation with respect to said phantom using the image parameters and the known geometric characteristics.

19. The method according to claim 18, further comprising:

displaying on a display the calculated sensor position and orientation.

20. The method according to claim 18, wherein the step of acquiring comprises:

acquiring a cross sectional image of the known structure.

21. The method according to claim 18, wherein the step of acquiring comprises:

acquiring a partial volume image of the known structure.

22. The method according to claim 18, wherein the known structure comprises a number of planes of material embodied within said ultrasound phantom.

23. The method according to claim 22, wherein the set of at least one predetermined geometric characteristic includes a distance between at least two of said number of planes and an angle between at least two of said number of planes.

24. The method according to claim 22, wherein the step of processing the image includes measuring a distance between at least two of said number of planes and measuring an angle between at least one of said number of planes and a reference line associated with a focal axis of the sensor.

25. The method according to claim 18 further comprising:
enhancing the calculation of sensor position and orientation by performing image de-correlation to detect small changes in sensor position and orientation.

26. The method according to claim 25 further comprising:
correcting for any error accumulations created by de-correlation by reevaluating the original calculation of sensor position and orientation.

27. The method according to claim 18 further comprising:
selecting said known structure from a number of known structures and retrieving from memory the set of at least one predetermined geometric characteristic that corresponds to the selected known structure.

* * * * *